United States Patent [19]
Mericle et al.

[11] Patent Number: 6,155,756
[45] Date of Patent: Dec. 5, 2000

[54] THREAD FORMING MACHINE FOR BONE MATERIAL

[75] Inventors: Robert W. Mericle, Eden, N.C.; Arthur A. Gertzman, Stony Point, N.Y.

[73] Assignee: Musculoskeletal Transplant Foundation, Edison, N.J.

[21] Appl. No.: 09/222,933

[22] Filed: Dec. 30, 1998

[51] Int. Cl.[7] .................................................. B23C 3/32
[52] U.S. Cl. .............................. 409/66; 409/66; 409/74; 606/73
[58] Field of Search ................................ 409/65, 66, 72, 409/74, 76, 77; 606/73, 76, 77

[56] References Cited

U.S. PATENT DOCUMENTS

| | | | |
|---|---|---|---|
| 1,384,913 | 7/1921 | Olson et al. | 470/81 |
| 1,442,483 | 1/1923 | Lee | 409/69 |
| 1,507,235 | 9/1924 | Hall | 409/66 |
| 2,214,058 | 9/1940 | Larsen | 10/102 |
| 2,791,822 | 5/1957 | Worrell | 29/37 |
| 3,579,686 | 5/1971 | Sorenson | 10/87 |
| 3,851,564 | 12/1974 | Kitano | 90/11.52 |
| 4,287,627 | 9/1981 | Chambers | 10/88 |
| 4,606,683 | 8/1986 | Link et al. | 409/66 |
| 5,221,234 | 6/1993 | Pakos | 470/10 |
| 5,250,007 | 10/1993 | Green | 470/11 |

*Primary Examiner*—Henry Tsai
*Assistant Examiner*—Adrian M. Wilson
*Attorney, Agent, or Firm*—John S. Hale; Gipple & Hale

[57] ABSTRACT

A machine for forming threads in a cylindrical bone dowel made of bone material, comprising a planar surfaced base provided with a threaded guide member having an externally threaded portion. A holding and rotating assembly is mounted on the base to rotatably hold the bone dowel so that the central axis of the bone dowel extends in the axial direction of the threaded guide member, An essentially planar support member is mounted on the guide member for movement with respect to base and an angle adjustment assembly is mounted to the support member. A cutting assembly having a cutting member in the form of a burr is also mounted on the support member so that when the threaded guide member is rotated the cutting assembly and associated cutting member is carried by support member to engage the bone dowel. A timing assembly is connected to the threaded guide member and the holding and rotating assembly so that when the cutting member moves along the bone dowel in an axial direction, the holding and rotating assembly rotates the bone dowel allowing a thread of a predetermined depth and configuration to be cut into the bone dowel.

27 Claims, 8 Drawing Sheets

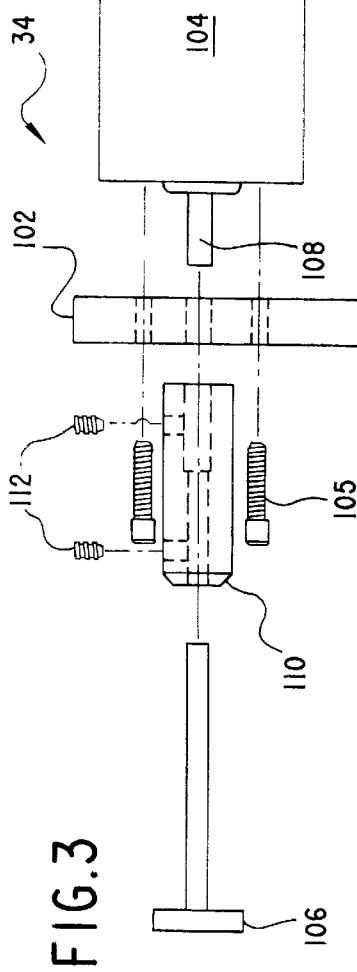
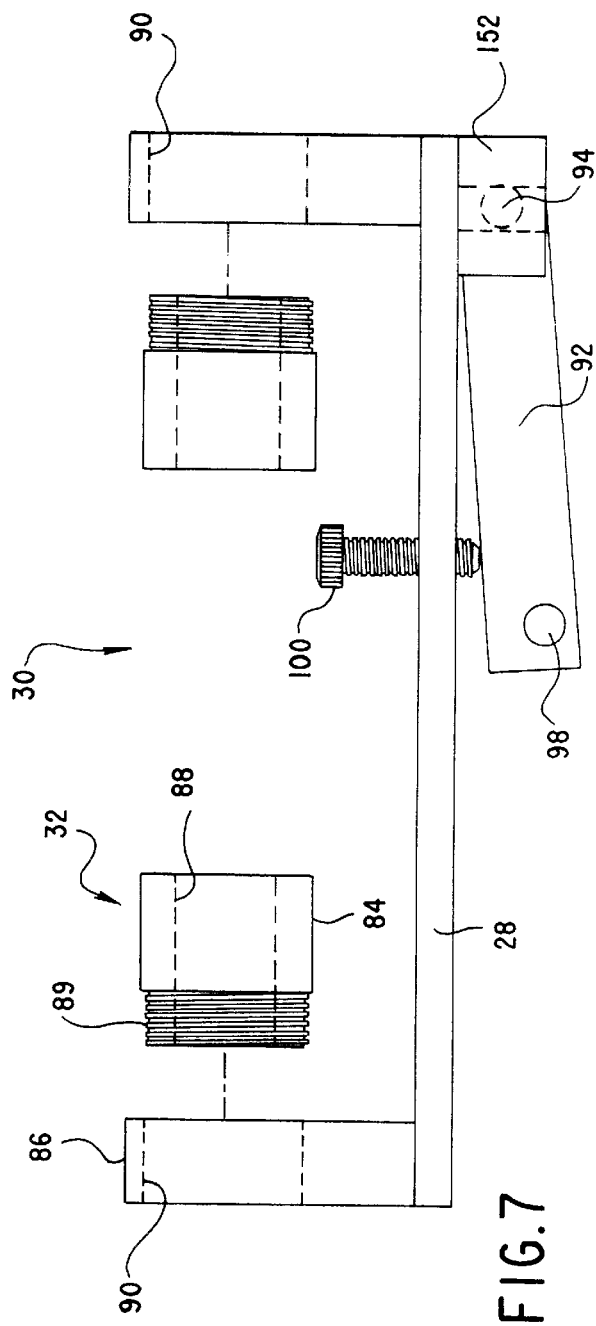

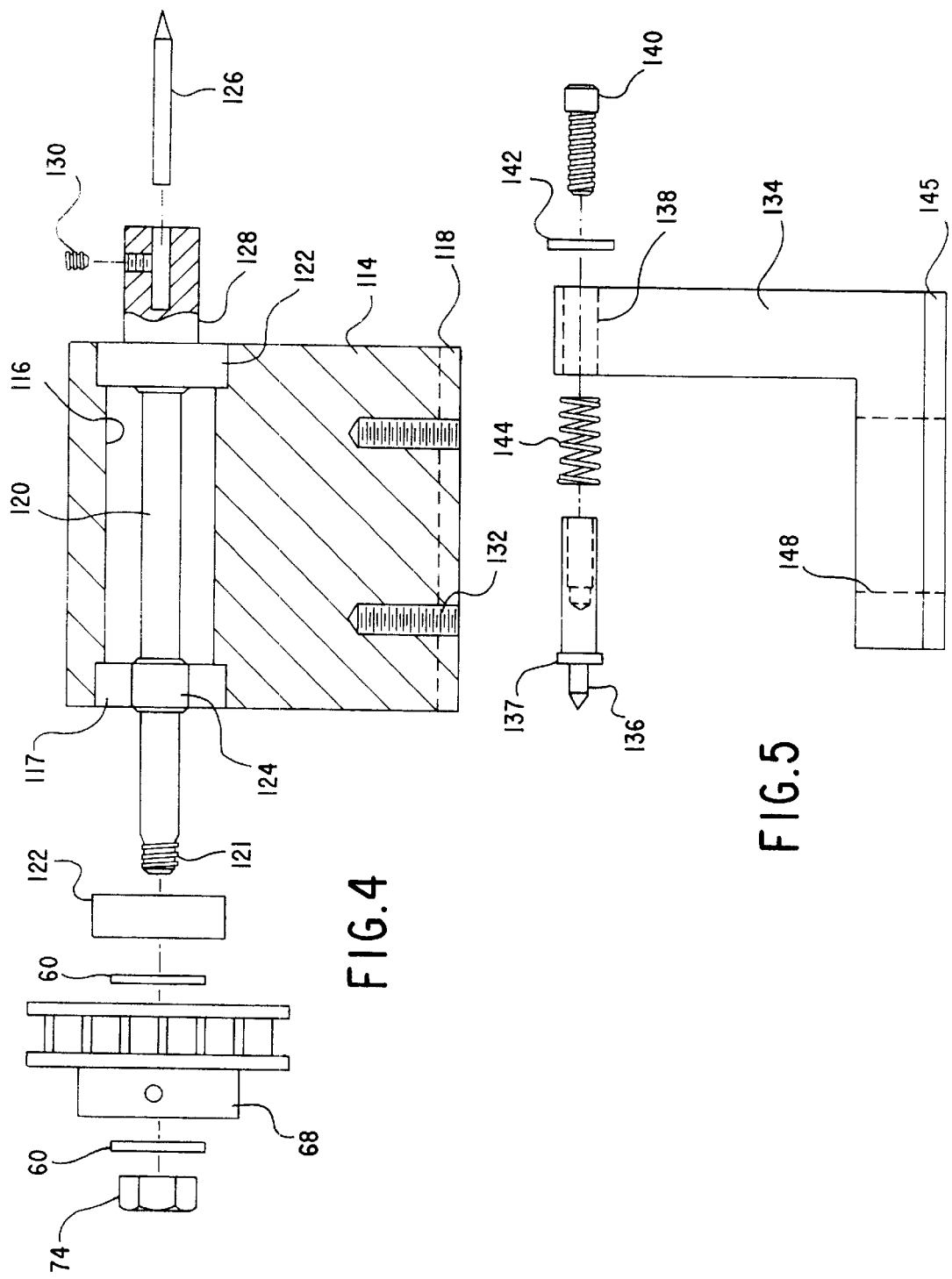

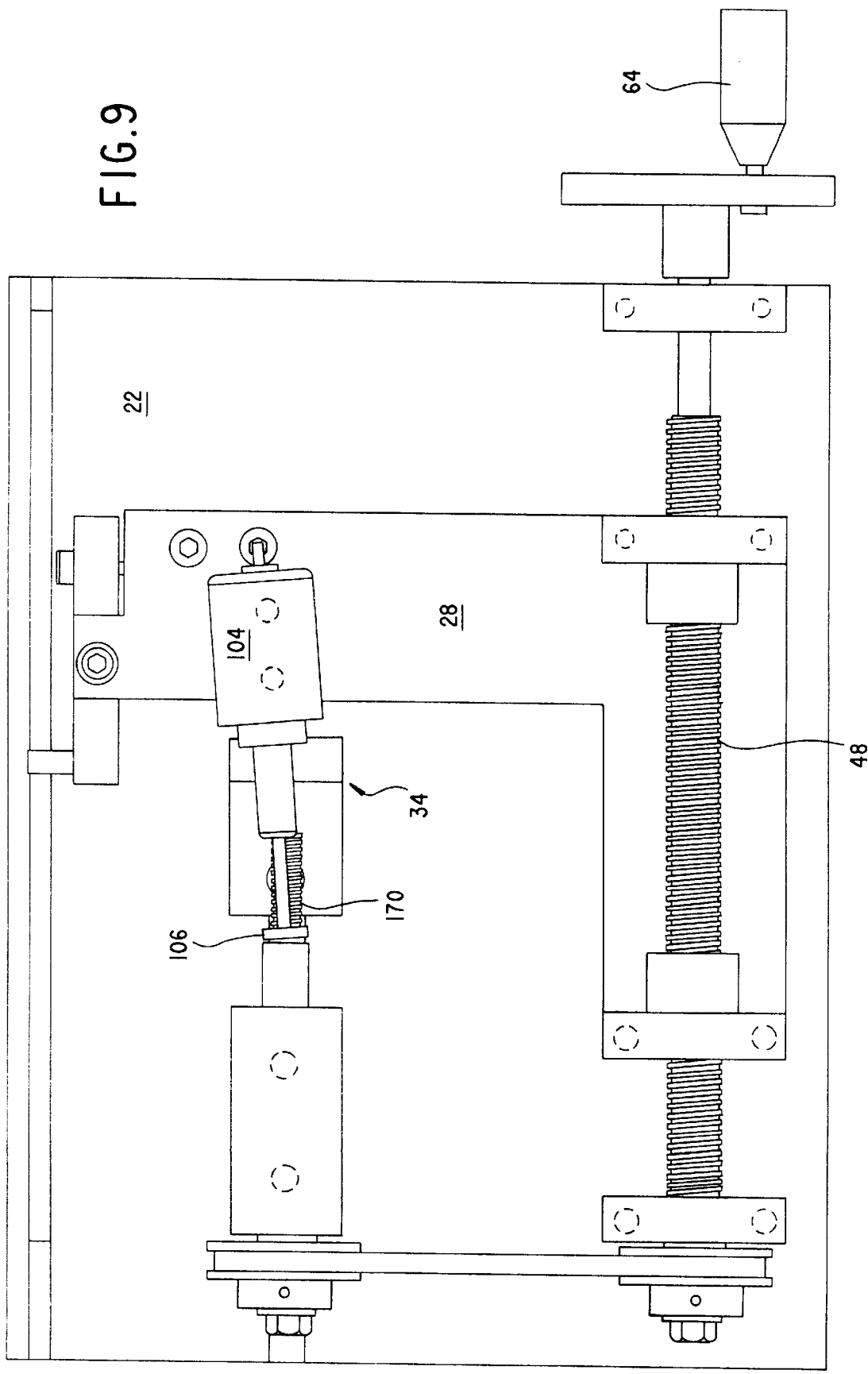

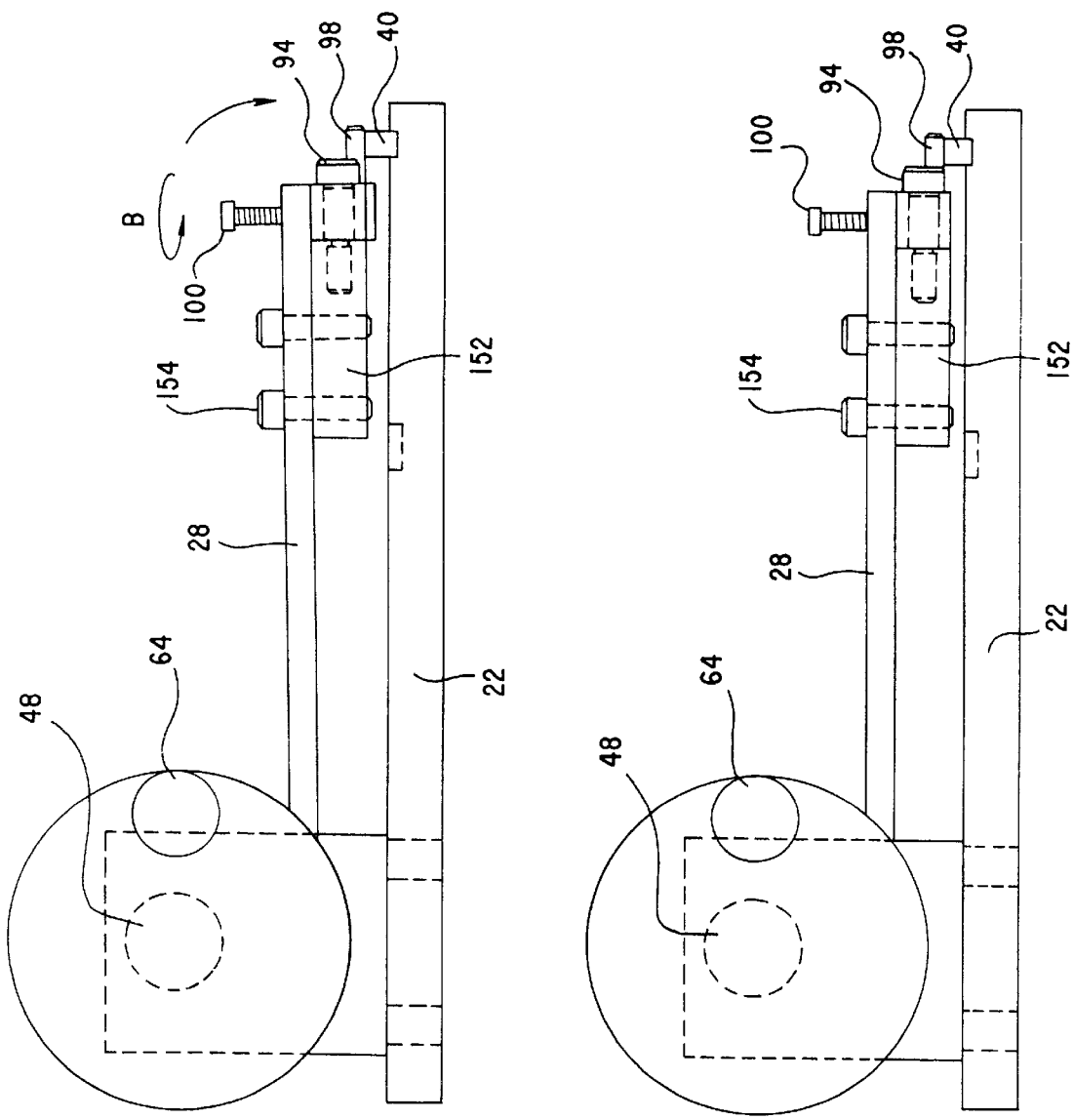

THREAD FORMING MACHINE FOR BONE MATERIAL

FIELD OF THE INVENTION

The present invention relates generally to a device for cutting threads on a blank work piece and more specifically towards a thread cutter for bone material in which the bone work piece is threaded into a screw.

BRIEF DESCRIPTION OF THE PRIOR ART

Cutting threads in bone material using conventional methods and existing machinery such as, for example, conventional lathes or cutting dies, results in destruction of the bone material and frequently results in damaged and torn screw threads.

This prior art is replete with thread cutting machines. However, the use of angled cutting devices while simultaneously rotating the workpiece and moving the cutter head along the workpiece represents a smaller area of prior art which has some pertinence to the present invention.

One such device is U.S. Pat. No. 5,221,234 which discloses a cutting device to apply variably canted threads to a screw blank work piece. A conventional cutting lathe is provided with a conventional hydraulically operated adjustable cutting support and a guide plate is mounted on the lathe adjacent the armature to produce a particular pattern in the work piece. The armature is pivotable to permit cutting at particular angles into the surface of the work piece. A secondary guide rigidly mounted to the cutting armature is utilized in producing a controlled variable pivot of the cutting armature during its progression along the body of the work piece. The cutting armature is moved longitudinally along the axis of the work piece rotating about its pivot point to create a change in the cutting angle over the length of the workpiece screw blank. In order to produce the variably canted threads on a screw body having a tapered core, a preliminary cutting is first performed on the screw blank and the cutting depth of the armature is changed over the course of the cutting operation thus permitting the combination of the tapered core of the screw body and the variable canted threads.

U.S. Pat. No. 5,250,007 discloses an apparatus and method for forming a thread of varying pitch by utilizing a threading assembly which includes a plurality of threading elements having thread cutters for engaging the work piece at different locations, with the threading assembly and work piece being driven both rotatively and at the same time axially relative to one another to form the thread. The rate of axial advancement per revolution between the work piece and each of the threading elements is varied, and the elements of the assembly are also shifted axially relative to one another during the rotary and axial movement, to give the thread its varying pitch.

U.S. Pat. No. 4,287,627 discloses a dowel threading device with a conventional router having a horizontal base with a vertically disposed cutting bit extending downwardly and outwardly from the base. A dowel threading attachment is secured underneath the base and has a vertically disposed bore adapted to receive the lower end of the cutting bit. A horizontal bore extends through the base and is in communication with the vertically disposed bore. The invention is operated by inserting a dowel into the end of the unthreaded horizontal bore, rotating the dowel about its horizontal axis as the dowel moves into contact with the rotating cutting bit, and engaging the threaded end of the dowel with the threaded portion of the horizontal bore so that the further longitudinal movement of the dowel through the bore will be controlled by the engagement of the dowel with the threaded portion of the horizontal bore.

U.S. Pat. No. 3,579,686 discloses an automatic screw machine with a pulley-driven collet and spindle assembly for reciprocally moving parts into and out of contact with boring tools. The assembly has two rearwardly extending rods which fit slidably within receptive openings in a drive pulley to permit its axial reciprocation while being driven by the pulley. The screw machine has an index rod and an index plate with receptive holes for the rod. The plate is affixed to a cam-controlled shaft to which a tool holder is also affixed. When the index rod is moved into one of the holes in the plate, a part held by the collet and spindle assembly is guided to a particular tool on the tool holder.

U.S. Pat. No. 2,791,822 discloses an automatic turret lathe of the kind in which the axis of the turret is arranged parallel to the axis of a bar or stock which is fed forward at intervals so that machining operations may be carried out on the end of the bar, the component thus formed being then parted from the bar. The turret is mounted so that it may be rotated to any one of a number of positions in which the turret stations are brought in succession into line with the axis of the bar so that a tool carried by the turret station carries out a cutting operation on the rotating bar. After each operation is completed, the turret is withdrawn, rotated to a new position with a different turret station coinciding with the axis of the bar and locked in position while a further operation is carried out.

U.S. Pat. No. 2,214,058 discloses an invention relating to cutting screw threads on a cylindrical body, such as a bar or rod.

Another U.S. Pat. No. 1,384,913 discloses a machine adapted to generate a plain helical thread upon a cylindrical blank. The cutter is in the general form of a gear wheel, that is, the cutting teeth are identical in form and are symmetrically located with respect to the cutter axis. In addition to its rotary movement, the cutter has a bodily movement in which the center of the cutter travels parallel to the axis of the work. This is accomplished by mounting the cutter upon a traveling carriage with the travel being produced by the rotation of a feed screw. The cutter is rotated about its axis by means of positive acting mechanism consisting of a worm gear rigidly connected with the cutter and cooperating with a worm or lead screw. This lead screw is capable of rotating about its axis but is otherwise stationary. In producing threaded objects, the lead screw rotates, and the worm gear is driven by the lead screw at the same time that it rolls along it. The cutter is mounted in a rocking frame and a cam is provided for rocking the frame to reciprocate the cutter toward and from the work piece to produce the relief of the teeth thereof. The pitch diameter of the cutter is substantially equal to the pitch diameter of the worm gear; also that the axis of the worm or lead screw is also the axis of oscillation of the rocking frame.

Prior cutting devices have not been able to be successfully used on bone material which because of its unique composition presents cutting problems.

SUMMARY OF THE INVENTION

A machine and method are described for forming a bone screw from a bone dowel with a rotating cutting member that is rotating at a first rotational speed in a rotational plane that is angled with respect to the central axis of the bone dowel to correspond to the desired angle of the screw threads to be formed in the dowel. The threads are formed on the bone dowel by moving the cutting member axially with respect to the bone dowel while simultaneously rotating the bone dowel about its central axis at a rotational speed that is less than the rotational speed of the cutting member.

This method of forming a thread on bone material by rotating the bone dowel and the cutting member at different rates is accomplished by the present thread forming machine provided with a rotatable threaded guide member. The threaded guide member is mechanically linked to an assembly that holds and rotates the bone dowel and is linked to a rotating cutting member so that when the threaded guide member is rotated, the cutting member moves axially with respect to the bone dowel while the bone dowel is simultaneously rotated. The threaded guide member links the bone dowel and the cutting member such that the axial displacement of the cutting member is directly proportional to the angular displacement of the bone dowel about its axis.

The thread forming machine is rotatably mounted on a base so that the central axis of the threaded guide member extends in an axial direction of the thread forming machine. A support member is movably mounted on the base and threadably engages the threaded guide member so that when threaded guide member is rotated, the support member moves axially. A bone dowel is held in a holding and rotating assembly that is mounted to the base and a timing assembly rotationally couples the holding and rotating assembly with the threaded guide member. Rotation of the threaded guide member moves the support member axially and simultaneously rotates the bone dowel so that the angular displacement of the bone dowel is directly proportionally to the axial displacement of the support member.

A cutting member is mounted on the support member and is positioned to form a helical thread on the slowly rotating bone dowel as the support member moves axially. An angle adjustment assembly is provided on the support member to adjust the radial distance of the cutting member from the central axis of rotation of the bone dowel to gradually form the thread in the bone dowel over several passes. This assembly controls the cutting depth of the cutting member during a given pass of the cutting member over the bone dowel which allows the machine operator to vary the cutting depth of the cutting member to gradually form a helical groove in the bone material over several cutting passes. This gradual deepening of the helical groove which defines the screw thread minimizes damage to the bone material. A camming surface is optionally provided on the base to radially move the support member as the support member moves axially to form a bone screw with a taper, a point or a similar screw profile.

Because of the friability and granular constancy of bone material, threads must be cut using a grinding or multi-toothed burr rotating at a high speed that is fed gradually radially inwardly into a slowly rotating bone part or bone dowel.

The thread forming machine may optionally be provided with a camming surface or guide structure that varies the radial distance of the cutting member from the central axis of the bone dowel as the cutting member moves in an axial direction to form a bone screw having a desired profile. The camming surface cams the cutting member radially to form a pointed or tapered bone screw profile from a cylindrical bone dowel.

It is an object of the present invention to provide a thread forming machine for forming a helical thread on a bone dowel or bone part comprised of bone material to form a bone screw which operates by rotating the bone material at a first, relatively slow rotational rate and rotating the cutting member at a second, relatively high rotational rate.

It is a further object of the invention to provide a thread forming machine that forms a helical groove in bone material using a rotating burr that rotates at a high rotational rate in a plane that corresponds to the desired thread angle in a slowly rotating bone dowel or bone part.

It is another object to provide a machine that can form a helical bone thread in bone material by gradually reducing the radial distance of the cutting member from the axis of the rotating bone dowel to gradually form a helical thread in the bone over several successive passes.

Another object of the invention is to provide a bone thread forming machine that provides a threaded guide member to guide the rotating cutting member axially and simultaneously rotate the bone dowel an angular distance that is directly proportional to the axial displacement of the cutting member to form a bone screw having a helical thread which has the same pitch as the pitch of a thread on the threaded guide member.

It is also an object of the invention to provide a thread forming machine that forms a helical thread in bone material using a rotating burr that has a profile identical to the profile of the helical thread formed by the rotating burr or cutting member.

It is a further object of the invention to provide a thread forming machine that is provided with a camming surface or guide structure to form a bone screw from a bone dowel such that the bone screw has the desired bone screw profile.

These and other objects, advantages, and novel features of the present invention will become apparent when considered with the teaching contained in the detailed disclosure along with the accompanying drawings.

BRIEF DESCRIPTION OF THE DRAWINGS

FIG. 3 is an enlarged exploded elevational view of the cutting assembly of the invention in isolation;

FIG. 4 is an exploded cross sectional view of a portion of a holding and rotating assembly taken through the line 4'—4' in FIG. 1;

FIG. 5 is an exploded view of a portion of the holding and rotating assembly;

FIG. 7 is a side elevational view of the support member taken along line 7'—7' of FIG. 6 showing the plurality of engagement members in exploded relation to the respective supports and showing an adjustment member of the angle adjustment assembly in a pivoted position of adjustment with respect to the support member;

FIG. 9 is a top plan view of a thread forming machine similar to the view of FIG. 8 showing the support member displaced in an axial direction from the first position;

FIG. 10 is an end view of the thread forming machine showing the angle adjustment assembly in a first position of adjustment; and FIG. 11 is an end view of the thread forming machine similar to the view of FIG. 10 showing the angle adjustment assembly in a second position of adjustment.

DETAILED DESCRIPTION OF THE PREFERRED EMBODIMENT

Figure 1:
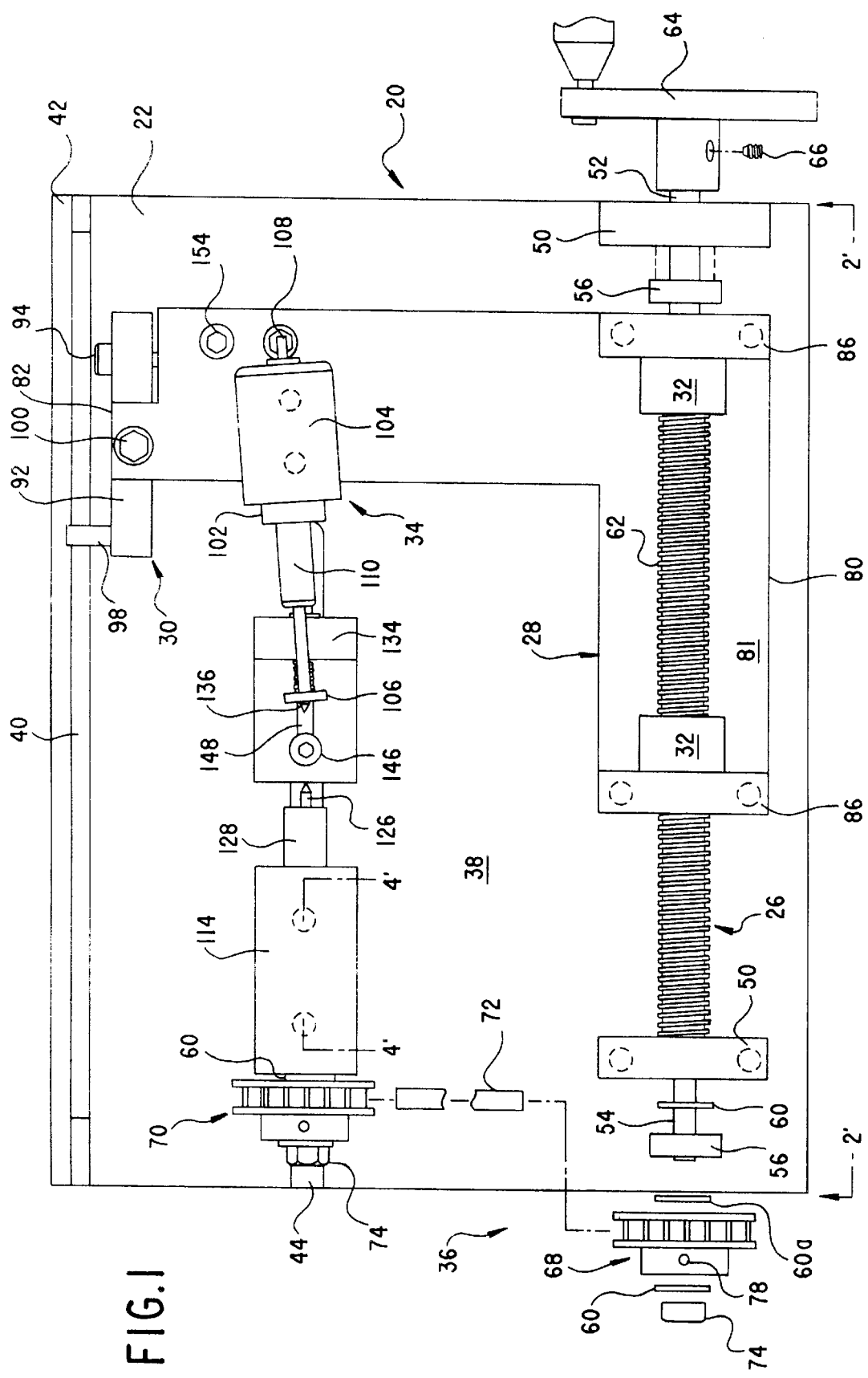
FIG. 1 is a top plan view of a thread forming machine of the invention showing a timing assembly in partially exploded view.
Figure 2:
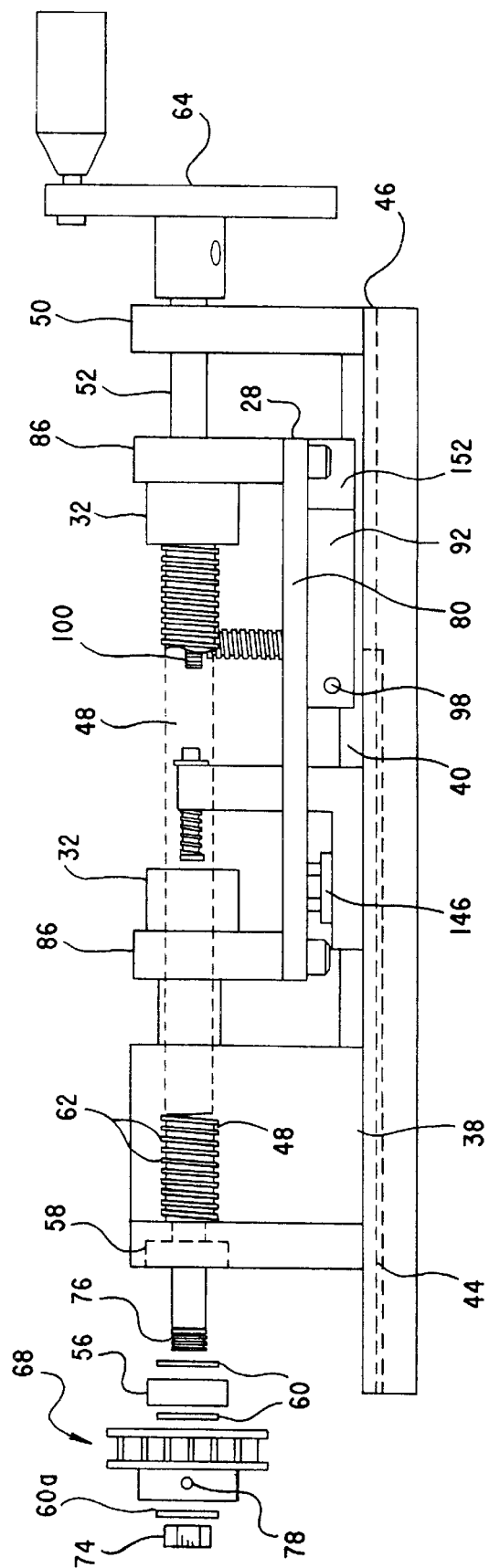
FIG. 2 is a side elevational view of the thread forming machine of FIG. 1 with a cutting assembly removed and showing a portion of the timing assembly in exploded view and a threaded guide member in phantom.

The preferred mode and best embodiment of the invention is shown in FIGS. 1–11. FIG. 1 shows a top plan view of a bone thread forming machine 20 and FIG. 2 shows a side elevational view of the machine 20 along the line 2'—2' indicated in FIG. 1. The thread forming machine 20 is constructed with a base or platform 22, a work piece holding and rotating assembly 24, a guide assembly 26, a support member 28, an angle adjustment assembly 30, a plurality of engagement members 32, a cutting assembly 34 and a timing assembly 36.

The base 22 is generally planar and preferably constructed of aluminum with a natural aluminum finish. The guide assembly 26 is mounted on a planar surface 38 of the base 22. The holding and rotating assembly 24 is mounted in a groove 44 in the central portion of the base 22.

The guide assembly 26 is constructed with a threaded guide member 48 rotatably mounted in upright guide holding support members 50 which are rigidly mounted to the base 22. The upright guide holding support members 50 rotationally support a smooth surfaced cylindrical first end 52 and second end 54 of the threaded guide member 48. The upright support guide holding members 50 are preferably made of aluminum and are secured to the base 22 by bolts. The threaded guide member 48 is preferably made of stainless steel and is rotationally mounted using conventional bearing assemblies 56 shown in FIGS. 1–2. The bearing assemblies 56 are mounted within a stepped throughgoing bore 58 in each guide holding member 50 as shown in phantom in FIG. 2. A stepped portion of the bore 58 is sized to receive and seat the bearing assembly 56 and a conventional washer 60. The portion of the exterior of the threaded guide member 48 between the guide holding members 50 is externally threaded with threads 62. A handle 64 is mounted on the first end 52 of the threaded guide member 48 by an Allen screw 66 so that when the handle 64 is rotated, the threaded guide member 48 rotates in the bearing assemblies 56 seated within the guide holding members 50.

The timing assembly 36 is constructed with a first timing mechanism 68 and a second timing mechanism 70. These mechanisms may be conventional timing belt pulleys mounted to the guide assembly 26 and the work piece holding and rotating assembly 24, respectively. The timing mechanisms 68 and 70 are rotationally coupled by a conventional timing belt 72 shown in fragmentary and exploded view in FIG. 1. The first timing mechanism 68 is secured to the end 54 of the threaded guide member 48 by a conventional nut 74 which engages end threads 76 of the threaded guide member 48. Washers 60 are mounted between the first timing mechanism 68 and the bearing assembly 56 and another washer 60a is mounted between the nut 74 and the first timing mechanism 68.

In the timing mechanism 68, the nut 74 and the washers 60 and 60a are shown in exploded view in FIG. I and 2. An Allen screw 78 on the first timing mechanism 68 secures the first timing mechanism 68 to the end 54 of the threaded guide member 48 so that the first timing mechanism 68 rotates with the threaded guide member 48.

The support member 28 or plate is mounted above base 22 and is generally L-shaped with a planar upper surface and is preferably constructed of aluminum with a natural aluminum finish. A pair of engagement members 32 are mounted to upright standards 86 secured to the support member 28. The angle adjustment assembly 30 is mounted to one of the legs of the support member 28. Each engagement member 32 is comprised of an internally and externally threaded tubular body 84 removably mounted to a support standard 86 by screwing the external threaded end 89 into same. Each tubular body 84 has an internally threaded bore 88 configured to receive and threadably engage the exterior thread 62 of the threaded guide member 48 and each support standard 86 has a throughgoing threaded bore 90 axially aligned with the threaded bore 88 of the tubular body 84. The threaded end 89 of the tubular body is screwed into the threaded bore 90 of the support standard 86.

As seen in FIG. 7, the angle adjustment assembly 30 is constructed with an adjustment member 92 pivotally mounted to the support member 28 by a pivot screw 94 that extends through a proximal end of the adjustment member 92 and block 152. A follower member 96 is mounted to a distal end of the adjustment member 92 by a pin 98. An angle adjustment screw 100 extends through a threaded bore in the support member 28 and engages the adjustment member 92 so that when the angle adjustment screw 100 is turned, the adjustment member 92 pivots on pin 94 with respect to the support member 28.

The L-shaped support member 28 is movably mounted on the base 22 by the threaded engagement between the engagement members 32 on leg 81 of the support member 28 with the threaded guide member 48 and by the sliding engagement of the follower member 96 with the rail 40 formed on base 22.

The cutting assembly 34 is mounted on a central portion of leg 82 of the support member 28. As shown in FIG. 3, the cutting assembly 34 consists of a motor mount 102 secured to the support member 28 by bolts, an electric motor 104 secured to the motor mount 102 by threaded fasteners 105 (bolts) and a rotating cutting member 106 which is coupled to a drive shaft 108 of the motor 104 by a chuck 110 with Allen screws 112. The cutting member 106 preferably is a grinding burr or a multi-toothed burr that is shaped to provide the desired thread profile of the bone screw.

The details of the construction of the work piece holding and rotating assembly 24 are shown in FIGS. 4–5 which show the assembly 24 in isolated and partially exploded view. The assembly 24 is formed by a support block 114 preferably constructed of aluminum which defines a throughgoing bore 116 with stepped end segments 117 and a bottom rib 118. A rotatable shaft 120 is rotatably mounted in the support block 114 by bearings 122 (shown schematically) that engage bushings 124. A work piece attachment member 126 is mounted in an end section 128 of the rotatable member 120 by an Allen screw 130. The support block 114 is mounted to the base 22 by bolts that extend through bores (not shown) in the base 22 into threaded bores 132 formed in the support block 114. When the support block 114 is mounted to the base 22, rib 118 is positioned within the central groove 44 to properly align the support block 114 with respect to the holding mechanism 134 and the cutting assembly 34. The second timing mechanism 70 is mounted to a threaded end 121 of the rotatable member 120 using washers 60 and the nut 74 to drive shaft 120.

As shown in FIG. 5, a holding mechanism 134, also preferably constructed of aluminum, holds an attachment member 136 mounted in a bore 138 cut in the holding mechanism with a bolt 140 and a washer 142. The attachment member 136 is biased outwardly toward the first attachment member 126 by a coil spring 144. The coil spring 144 is seated against a collar 137 integrally formed on the attachment member 136 with the other end engaging an outer surface of the body of the holding mechanism 134. The holding mechanism 134 has a bottom rib 145 and which is mounted to the base 22 by placing rib 145 in the central groove 44 of the base 22 and is secured by tightening a bolt 146 that extends through an aperture 148 formed in the base 135 of the holding mechanism 134 to threadably engage a threaded bore (not shown) in the base 22. The holding mechanism 134 can be linearly moved with respect to the support block 114 to accommodate bone dowels of various lengths by loosening the bolt 146, sliding the holding structure 134 within the groove 44 toward or away from the support block 114 and retightening the bolt.

Figure 6:
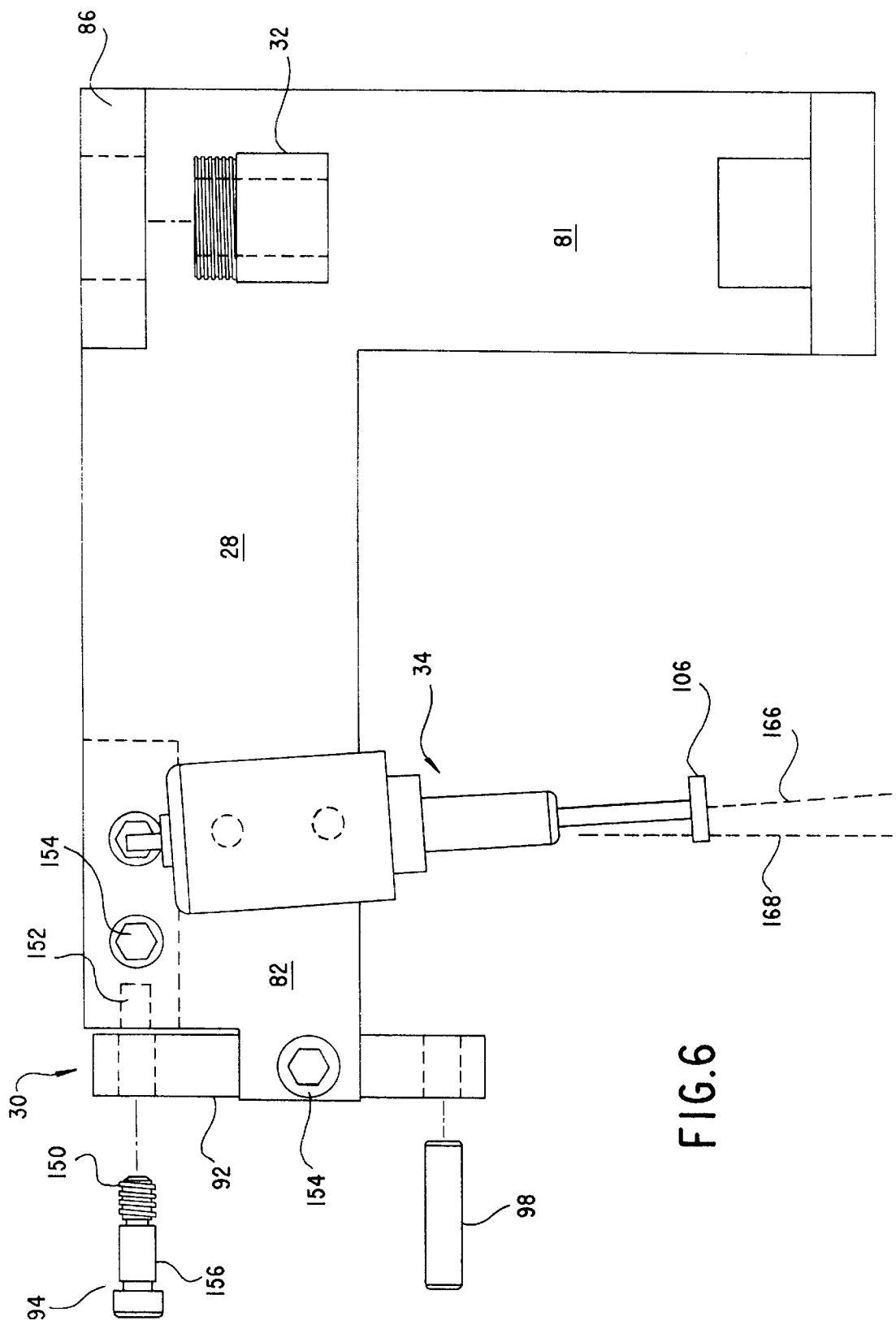
FIG. 6 is a top plan view of a support member of the thread forming machine showing a pivot screw, a pin and a follower member of an angle adjustment assembly in exploded view and showing a plurality of engagement members in exploded relation to a plurality of support members.

FIG. 6 is an enlarged top plan view of the support member 28 and a plurality of structures attached to the support member 28 in isolation. This figure shows the construction of the angle adjustment assembly 30 in partially exploded view and shows one engagement member 32 in exploded view with respect to the support member 86. The pivot screw 94 has a threaded distal end 150 that threadably engages a support block 152 which is mounted to the support member 28 by bolts 154. The support block 152 is shown in phantom lines in FIG. 6, but is better seen in FIGS. 7, 10 and 11. The adjustment member 92 pivots about the smooth central portion 156 of the pivot screw 94. The follower pin 98 is shown in exploded relation with the distal end of the adjustment member 92. While the follower pin 98 is cammed by rail 40, a groove and wheel or pin can be substituted.

FIG. 7 shows a side view of the support member 28 similar to the top plan view of FIG. 6 except that the cutting assembly 34 has been removed to more clearly show details of the angle adjustment assembly 30. More specifically, it can be appreciated from FIG. 7 that as the angle adjustment screw 100 is turned, it threadably advances with respect to the support member 28 and causes the adjustment member 92 to pivot about the pivot screw 94 with respect to the support member 28.

OPERATION OF THE THREAD FORMING MACHINE

Figure 8:
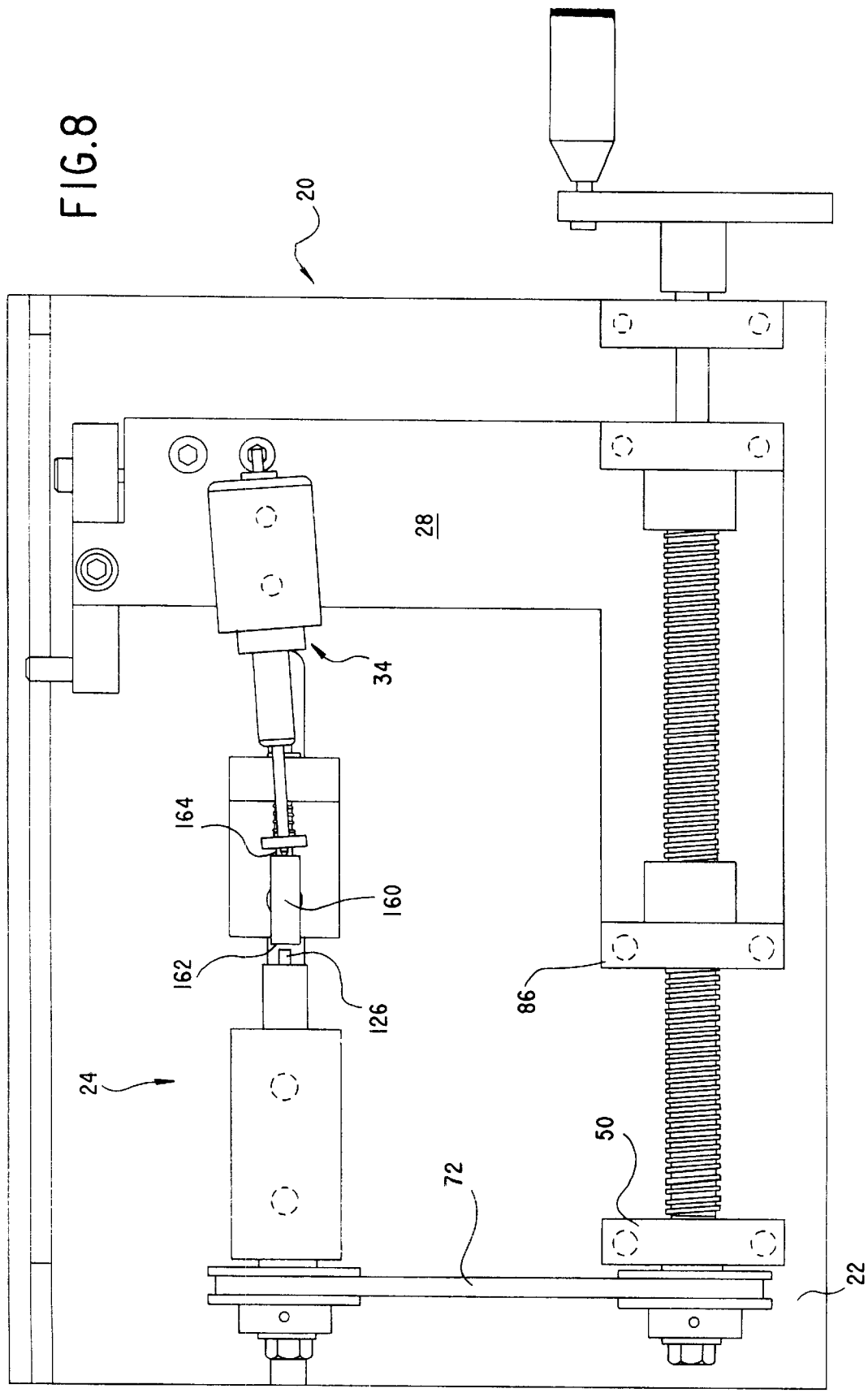
FIG. 8 is a top plan view of the thread forming machine similar to the view of FIG. 1 showing a bone dowel mounted therein and showing the support member in a first position.

The operation of the thread forming machine 20 can be understood by examining FIGS. 8–11. FIG. 8 shows an embodiment of the thread forming machine 20 constructed to form a helical thread on a bone dowel 160 shown mounted in the holding and rotating assembly 24. The bone dowel 160 is an essentially cylindrical structure comprised of bone material and has a first end 162, a second end 164 and a central axis of symmetry extending between the two ends. The bone dowel 160 is rotatably mounted in the holding and rotating assembly 24 by securing the ends 162, 164 to the first and second attachment members 126, 136, respectively. The attachment members 126, 136 are axially aligned and hold the bone dowel 160 so that the dowel rotates about its central axis and the central axis is essentially parallel to the central axis of the threaded guide member 48.

It can be understood, therefore, that the thread forming machine 20 can be regarded as having an axial direction defined by the axis of the bone dowel 160 and that this axis and the axis of the threaded guide member 48 both extend in the axial direction of the thread forming machine 20. When the threaded guide member 48 is rotated using the handle 64, the support member 28 and the structures mounted on the support member 28 move in an axial direction. It can be appreciated from FIG. 2 that the leg 81 of the support member 28 is supported by the threaded guide member 48 and the opposite leg 82 of the support member 28 is supported by the follower pin 98 and the adjustment arm 92. When the threaded guide member 48 rotates, the engagement members 32 are carried axially along the threaded guide member 48 and the follower pin 98 moves axially along rail 40 or a groove (not shown).

The cutting member 106 rotates at a first relatively high rotational speed in a rotational plane that is angled with respect to the central axis of the bone dowel 160 to correspond to the desired angle of the helical thread formed in the bone material. The rotating shaft is at an angle of approximately four degrees with the central axis of the bone dowel 160 and therefore the axial direction of the machine 20 as best seen in FIG. 6 where the axis of rotation of the cutting member 106 is labeled 166 and the axial direction is represented by a dashed line labeled 168.

The bone dowel 160 is mounted in the holding and rotating assembly 24 by moving the second attachment member 136 away from the first attachment member 126 which compresses the coil spring 144 and allows the bone dowel 160 to placed between the members 126, 136.

To form threads in a bone dowel 160, the electric motor 104, which is attached to a power source (not shown), is energized to rotate the cutting member 106 at a relatively high rotational speed and the associated threaded guide member 48 is rotated in an appropriate rotational direction to move the support member 28 and the cutting member 106 which is mounted on it axially towards the bone dowel 160. It can be appreciated from FIG. 8 that because the first and second timing mechanisms 68, 70 are interconnected by the timing belt 72, when the threaded guide member 48 rotates, the rotatable member 120 simultaneously rotates which causes the rotation of the bone dowel 160 in the holding and rotating assembly 24.

As the cutting member 106 moves axially over the rotating bone dowel 160, it cuts a helical thread 170 on the exterior of the dowel. Because the rotating bone dowel 160 and the rotating cutting member 106 are engaged, the rotating cutting member 106 cuts a helical groove in the bone material to form a helical thread. The pitch of the formed thread is identical to the pitch of the helical thread on the threaded guide member 48.

Because of the friability and granular constancy of bone material, the helical thread must be cut using a grinding or a multi-toothed burr that is rotating at a relatively high rotational rate and that is gradually advanced into the bone material that is rotating at a relatively slow rate. The rotational rate of the bone dowel 160 while the groove is being cut may be constant or may be varied. Therefore, it can be understood that because the axial movement of the cutting member 106 and the rotation or angular movement of the bone dowel 160 are linked or slaved together by the timing assembly 36, the axial movement of the rotating cutting member 106 may therefore be constant or varied as well. It can be appreciated from FIG. 2 that the position of the adjustment member 92 determines the radial distance of the cutting member 106 from the bone dowel 160. Adjusting the angle adjustment assembly 30, therefore, changes the cutting depth of the cutting member 106. Because of the nature of bone material, it is desirable to form the helical thread by passing the cutting member 106 over the bone dowel 160 several times at successively smaller radial distances to gradually form a helical thread of the desired depth.

For example, to gradually form a thread in bone material, the angle adjustment assembly 30 may be adjusted to position the cutting member 106 at a first radial distance when the cutting member 106 is in the position shown in FIG. 8. The cutting member 106 may then be advanced axially over the rotating bone dowel 160 to the position shown in FIG. 9 by rotating the handle 64 in a first rotational direction and the cutting member 106 can then be returned to the position shown in FIG. 8 by rotating the handle 64 in an opposite rotational direction. The machine operator can then adjust the angle adjustment screw 100 to decrease the radial distance of the cutting member 106 from the bone dowel 160 and the cutting member 106 can be reciprocated axially over the bone dowel 160 to gradually increase the helical groove depth. This procedure can be repeated until the desired thread height is attained.

FIGS. 10 and 11 illustrate the operation of the angle adjustment assembly 30 to adjust the radial distance of the cutting member 106 from the bone dowel 160. It can be appreciated from FIG. 10 that the cutting assembly 34 (not shown) is at a first radial height and that by rotating the screw 100 in the direction indicated by an arrow B, the support member 28 pivots downwardly with respect to the base 22 to decrease the radial distance of the cutting member 106.

It can also be understood from FIGS. 10 and 2 that as the cutting member 106 moves axially, the follower member 96 slides along rail 40. An upper surface of the rail 40 forms a camming surface which can be configured to change the radial distance of the cutting member 106 from the central axis of the bone dowel 160 as the rotating cutting member 106 moves axially.

In the present embodiment, the camming surface is parallel to the axial direction and is essentially planar and parallel to the axis of the bone dowel 160. Therefore, this camming surface does not change the radial distance of the cutting member 106 from the bone dowel 160 as the cutting member 106 moves axially. The thread forming machine is thus configured to form threaded cylindrical bone screws because the cam profile of the camming surface is planar and parallel to the axial direction. This camming surface can be altered, however, to permit cutting a helical thread on pointed straight screws or to permit cutting more complex thread shapes or screw profiles such as screws having tapered, pointed screw profiles.

It can therefore be appreciated that the thread forming machine 20 is provided with two ways of changing the radial distal of the cutting member 106 from the bone dowel 160. The first way, using the screw 100, is preferably used to adjust the cutting depth of the cutting member 106 for a given pass over the bone dowel 160. The second, the profile of the camming surface, is used to form a bone screw having a desired profile.

The thread forming machine 20 illustrated in FIGS. 1–11 is exemplary and is meant to convey the broad principles of the invention. Because of the nature of bone material it is preferred to cut a helical groove in the bone material using a high speed rotating grinding or multi-toothed burr that is fed gradually into a slowly rotating bone dowel 160 or other bone part. The burr is shaped to the desired thread profile and the cutting member 106 rotates in a plane that corresponds to the desired angle or slope of the screw threads. The bone dowel 160 and the cutting member 106 may rotate in essentially the same direction or in essentially opposite directions.

The timing assembly 36 links the axial movement of the cutting member 106 with the angular movement of the bone dowel 160 such that the axial displacement of the cutting member 106 is directly proportional to the angular displacement of the bone dowel 160. The rotating cutting member 106 is mechanically connected to the threaded guide member 48 by support member 28 so that rotation of the threaded guide member 48 effects simultaneously the axial displacement of the cutting member 106 and the angular displacement of the bone dowel 160. Optionally a camming surface or other appropriate guide structure may be provided which guides the radial movement of the cutting member 106 as it is moved axially by the threaded guide member 48 to form a desired profile in the bone screw.

The angle adjustment assembly 30 can be constructed in many other ways to serve the same purpose. For example, any moving member adjustably mounted to the support member 28 can serve the same purpose as the pivotally attached adjustment member 92. It can be appreciated that the follower member 96 is simply a structure that follows the camming surface or groove guide and can be, for example, a wheel or similar structure. Similarly, the construction of the timing assembly 36 is exemplary and any suitable structure can be used to rotationally couple the threaded guide member 48 and the holding and rotating assembly 24. For example, the timing belt and pulleys can be replaced by a plurality of gears. The holding and rotating assembly 24 is also exemplary and can be comprised of a conventional head stock and tailstock assembly of the type used in conventional laths. The threaded guide member 48 may be rotated manually with the handle 64 or may be rotated bi-directionally with any suitable power source.

The holding and rotating assembly 24 and the angle adjustment assembly 30 allow thread formation on bone dowels of a wide range of lengths and diameters. It is also understood that although the bone dowel 160 illustrated in the drawings is initially cylindrical, the bone dowel 160 can initially be any appropriate shape such as fruscoconical.

The principles, preferred embodiment and modes of operation of the present invention have been described in the foregoing specification. However, the invention should not be construed as limited to the particular embodiment which have been described above. Instead, the embodiment described here should be regarded as illustrative rather than restrictive. Variations and changes may be made by others without departing from the scope of the present invention as defined by the following claims:

We claim:

1. A method of forming a bone screw comprised of a bone material in the form of a bone dowel having a central axis, comprising the steps of:
    a) rotating a cutting member at a first rotational speed in a rotational plane that is angled with respect to a central axis of said bone dowel to correspond to the angle of the screw threads;
    b) cutting a thread in the bone dowel by transporting the rotating cutting member axially with respect to the bone dowel while simultaneously rotating the bone dowel about its central axis thereof at a rotational speed less than the first rotational speed, said axial movement of said cutting member being directly proportional to the angular displacement of the bone dowel, the directly proportional movement of the cutting member being effected by rotating a threaded guide member which effects simultaneously the rotation of the bone dowel and the axial movement of the cutting member and wherein the radial distance of the cutting member from the central axis is varied by guiding the radial movement of the cutting member with a guide structure as the cutting member moves axially.

2. A method of forming a bone screw comprised of a bone material as claimed in claim 1 wherein the rotational speed of the bone dowel is constant.

3. A method of forming a bone screw comprised of a bone material as claimed in claim 1 wherein step b) includes cutting a thread in a bone dowel a first depth; and adds an additional step c) cutting a thread in a bone dowel a second deeper depth by transporting the rotating cutting member axially with respect to the bone dowel while simultaneously rotating the bone dowel about the central axis thereof at a rotational speed less than the first rotational speed.

4. A method of forming a bone screw comprised of a bone material as claimed in claim 1 wherein the bone dowel and the cutting member rotate in opposite directions.

5. A method of forming a bone screw comprised of a bone material as claimed in claim 1 wherein the bone dowel and the cutting member rotate in the same direction.

6. A method of forming a bone screw comprised of a bone material as claimed in claim 1 wherein the radial distance of the cutting member from the central axis is constant to form a threaded cylindrical bone screw.

7. A method of forming a bone screw comprised of a bone material as claimed in claim 1 wherein the radial distance of the cutting member from the central axis is varied as the cutting member moves axially to form a pointed threaded bone screw.

8. A method of forming a bone screw from a bone dowel comprised of a bone material having a central axis, comprising the steps of:
   a) rotating a cutting member at a first rotational speed in a rotational plane that is angled with respect to a central axis to correspond to the angle of the screw threads;
   b) holding said bone dowel in a stationary linear position while rotating said bone dowel;
   c) cutting a thread at a first depth in the bone dowel by transporting the rotating cutting member axially with respect to the bone dowel by using the transporter for said cutting member to rotationally drive the bone dowel holder simultaneously rotating the bone dowel about its central axis at a rotational speed less than the first rotational speed; and
   d) cutting a thread at a second deeper depth in the bone dowel by transporting the rotating cutting member axially with respect to the bone dowel by using the transporter for said cutting member to rotationally drive the bone dowel holder simultaneously rotating the bone dowel about its central axis at a rotational speed less than the first rotational speed.

9. A thread forming machine for forming threads in a bone dowel comprised of bone material having a central axis to form a bone screw, comprising:
   a base assembly defining a planar surface and a camming surface;
   a bone dowel holding and rotating assembly mounted to said base for holding the bone dowel in an axial direction of the thread forming machine and rotating the bone dowel about a central axis;
   a guide assembly mounted on said base assembly;
   a support member moveably mounted on said guide assembly;
   an angle adjustment assembly mounted on the support member and moveably mounted for engagement with said camming surface of said base assembly;
   a cutting assembly mounted on the support member, said cutting assembly being provided with a cutting member for forming threads in the bone dowel, said support member being movably mounted on said guide assembly so that said guide assembly can move said support member in an axial direction moving the cutting member in the axial direction with respect to the bone dowel, said angle adjustment assembly moving the support member to determine the radial distance of the cutting member from the central axis of the bone dowel; and
   a timing assembly connected to the guide assembly and the bone dowel holding and rotating assembly so that when the guide assembly moves the cutting assembly in the axial direction, the holding and rotating assembly rotates the bone dowel at a speed that is directly proportional to the axial displacement of the cutting assembly.

10. A thread forming machine for forming threads in a bone dowel as claimed in claim 9, wherein said guide assembly comprises: a threaded guide member having threads on a portion of the exterior thereof that is rotatably mounted on said base so that the guide member is approximately axially directed and at least one engagement member mounted to said support member and engaging said threaded guide member, said at least one engagement member being threadably engaged with the threaded guide member so that the support member moves in an axial direction when the threaded guide member is rotated.

11. A thread forming machine for forming threads in a bone dowel as claimed in claim 9, wherein said holding and rotating assembly comprises a first holding structure mounted on the base, a rotatable member rotatably mounted in said first holding structure, a first attachment member secured to an end of the rotatable member for securing one end of the bone dowel to the rotating and holding assembly;
   a holding member mounted to said base, a second attachment member mounted on the second holding member for rotationally coupling the opposite end of the bone dowel to the second holding member wherein the first and second attachment members hold the bone dowel so that the central axis extends in the axial direction and the bone dowel moves an angular distance when the rotatable member is rotated.

12. A thread forming machine for forming threads in a bone dowel as claimed in claim 9, wherein said timing assembly comprises a first timing assembly mounted to the threaded guide member and a second timing assembly mounted to the rotatable member, the first and second timing assemblies being mounted so that when a guide member is rotated to move the support member axially the bone dowel moves angularly with respect to said cutting assembly.

13. A thread forming machine for forming threads in a bone dowel as claimed in claim 12, wherein the first timing assembly is a first pulley and the second timing assembly is a second pulley, with a timing belt mounted to and connecting said first and second pulleys.

14. A thread forming machine for forming threads in a bone dowel as claimed in claim 9, wherein said angle adjustment assembly comprises an adjustable member movably mounted on the support member so that when the adjustable member is moveably positioned relative to said support member, the radial distance of the cutting member from the central axis of the bone dowel changes.

15. A thread forming machine for forming threads in a bone dowel as claimed in claim 9 wherein said camming surface is a rail.

16. A thread forming machine for forming threads in a bone dowel as claimed in claim 9, wherein said angle adjustment assembly is pivotally mounted to said support member, said angle adjustment assembly comprising an arm connected to said support member, an angle adjustment screw mounted on the support member and engaged with the adjustment member so that rotating the angle adjustment screw pivots the arm with respect to the support member; and a following member mounted on the adjustment member and movably mounted on said camming surface so that when the support member moves axially, the following member follows the camming surface to move the cutting member radially as the cutting member moves axially.

17. A thread forming machine for forming threads in a bone dowel as claimed in claim 11, wherein the second holding structure is releasably mounted to said base so the second holding structure can be selectively positioned in an axial direction to accommodate bone dowels of different lengths and the second attachment member is spring biased toward the first attachment member so that a bone dowel can be easily mounted in the holding and rotating assembly.

18. A thread forming machine for forming threads in a cylindrical bone dowel made of bone material, comprising:
   a planar surfaced base;
   a threaded guide member having an externally threaded portion, a first end and a second end rotatably mounted on said base so that the threaded guide structure extends in the axial direction;
   a holding and rotating assembly mounted on said base rotatably holding the bone dowel so that the central axis thereof extends in the axial direction;
   a planar support member mounted on said guide member for movement with respect to said base;
   an angle adjustment assembly mounted to said support member;
   a cutting assembly having a cutting member in the form of a burr mounted on the support member;
   means to rotate said threaded guide member, said support member being mounted so that when the threaded guide member is rotated the cutting member carried by said support member moves in an axial direction; and
   a timing assembly connected to the threaded guide member and the holding and rotating assembly so that when the cutting member moves in an axial direction the holding and rotating assembly moves the bone dowel angularly.

19. A thread forming machine for forming threads in a cylindrical bone dowel as claimed in claim 18 wherein said cutting member is a grinding burr.

20. A thread forming machine for forming threads in a cylindrical bone dowel as claimed in claim 18 wherein said cutting member is a multi tooth burr.

21. A thread forming machine for forming threads in a bone dowel made of bone material as claimed in claim 18 further comprising a guide structure that extends in the axial direction mounted on the said base and wherein the angle adjustment assembly is mounted to said support member so that when the cutting member moves in the axial direction, the cutting member is guided radially to form a predetermined screw profile.

22. A thread forming machine for forming threads in a bone dowel made of bone material as claimed in claim 21 wherein the cutting member rotates in a cutting plane and said cutting assembly is mounted so that the cutting plane is angled with respect to the axial direction to correspond to a thread angle of the bone screw.

23. A thread forming machine for forming threads in a bone dowel made of bone material as claimed in claim 18 further comprising:
   a handle mounted on said threaded guide member, said holding and rotating assembly comprising a head stock assembly with a first holding structure mounted on said base and a rotatable member rotatably mounted in the first holding structure and having a first end and a second end; and a first attachment member secured to the second end of the rotatable member for mounting the first end of the bone dowel to the holding and rotating assembly; and
   a tailstock assembly comprising a second holding structure releasably mounted to said base allowing said second holding structure to be positioned in different axial distances to accommodate bone dowels of different lengths, a second attaching member mounted to the second holding structure for rotatably coupling the second of the bone dowel to the second holding structure.

24. A thread forming machine for forming threads in a bone dowel made of bone material as claimed in claim 18 wherein said angle adjustment assembly comprises a pivot arm pivotally mounted to said support member, an adjustment screw mounted to the support member and engaging the pivot arm so that when the adjustment screw is turned the pivot arm changes a radial distance of the cutting member from the bone dowel so that when the cutting member moves radially the sliding engagement moves the cutting member radially to form the predetermined screw profile.

25. A thread forming machine for forming threads in a bone dowel made of bone material as claimed in claim 18 wherein said timing assembly comprise a first pulley mounted to said threaded guide member, a second pulley mounted to the said rotatable member and a timing belt mounted to said first and second pulleys so that when the threaded guide member is rotated, the cutting member moves axially and the bone dowel moves angularly to form a thread in the dowel that has the same angle as the thread on the guide member.

26. The thread forming machine for forming threads in a bone dowel made of bone material as claimed in claim 23 wherein said cutting assembly comprises a motor mounted to the support member, a cutting member connected to a shaft of said motor, said cutting member comprising a burr rotatably mounted to the motor and having a shape that conforms a predetermined thread profile of the bone screw.

27. A thread forming machine for forming threads in a bone dowel comprised of bone material having a central axis to form a bone screw, comprising:
   a base defining a planar surface;
   a bone dowel holding and rotating assembly mounted to said base for holding the bone dowel in an axial direction of the thread forming machine and rotating the bone dowel about a central axis;
   a guide assembly mounted on said base;
   a support member moveably mounted on said guide assembly;
   an angle adjustment assembly mounted on the support member and engaging said base;
   a cutting assembly mounted on the support member, said cutting assembly being provided with a burr cutting member for forming threads in the bone dowel, said support member being movably mounted on said guide assembly so that said guide assembly can move said support member in an axial direction moving the burr cutting member in the axial direction with respect to the bone dowel, said angle adjustment assembly moving the support member to determine the radial distance of the burr cutting member from the central axis of the bone dowel; and a timing assembly connected to the guide assembly and the bone dowel holding and rotating assembly so that when the guide assembly moves the cutting assembly in the axial direction, the holding and rotating assembly rotates the bone dowel at a speed that is directly proportional to the axial displacement of the cutting assembly.

* * * * *